United States Patent [19]
Fournier, Jr. et al.

[11] Patent Number: 4,760,840
[45] Date of Patent: Aug. 2, 1988

[54] ENDOSCOPIC LASER INSTRUMENT

[75] Inventors: George R. Fournier, Jr., San Francisco; Andrew H. Kung, Moraga; Jack W. McAninch, Mill Valley, all of Calif.

[73] Assignee: The Regents of the University of California, Berkeley, Calif.

[21] Appl. No.: 942,362

[22] Filed: Dec. 16, 1986

[51] Int. Cl.$^4$ .............................................. A61B 17/36
[52] U.S. Cl. ..................................... 128/303.1; 128/6
[58] Field of Search ........................................ 128/4–8, 128/303.1, 395–398; 219/121 LQ, 121 LV

[56] References Cited

U.S. PATENT DOCUMENTS

| | | | |
|---|---|---|---|
| 3,279,460 | 10/1966 | Sheldon | 128/6 |
| 3,373,736 | 3/1968 | Fiore et al. | 128/6 |
| 4,072,147 | 2/1978 | Hett | 128/6 |
| 4,141,362 | 2/1979 | Wurster | 128/303.1 |
| 4,178,920 | 12/1979 | Cawood et al. | 128/6 |
| 4,301,790 | 11/1981 | Bol et al. | 128/6 |
| 4,313,431 | 2/1982 | Frank | 128/7 |
| 4,421,106 | 12/1983 | Uehara | 128/4 |
| 4,526,170 | 7/1985 | Tanner | 128/303.1 |
| 4,551,129 | 11/1985 | Coleman et al. | 128/303.1 |
| 4,592,353 | 6/1986 | Daikuzono | 128/303.1 |
| 4,610,242 | 9/1986 | Santangelo et al. | 128/4 |

FOREIGN PATENT DOCUMENTS

| | | | |
|---|---|---|---|
| 2828322 | 1/1980 | Fed. Rep. of Germany | 128/303.1 |
| 3209444 | 10/1982 | Fed. Rep. of Germany | 128/303.1 |
| 2385372 | 12/1978 | France | 128/303.1 |
| 1132906 | 1/1985 | U.S.S.R. | 128/6 |

OTHER PUBLICATIONS

Staehler, et al., "Endoscopy in Experimental Urology Using an Argon-Laser Beam", 1976, pp. 1-4 (Endoscopy).

Willscher, et al., "Development of a Carbon Dioxide Laser Cystoscope", 1978, pp. 202-207 (The Journal of Urology).

Bulow, et al., "Transurethral Laser Urethrotomy in Man: Preliminary Report", 1979, pp. 286, 287 (The Journal of Urology).

Andrews, Jr., et al., "Bronchhoscopic $CO_2$ Laser Surgery", 1980, pp. 35-45 (Lasers in Surgery and Medicine).

Tadir, et al., "Hysteroscope for $CO_2$ Laser Application", 1984, pp. 153-156 (Lasers in Surgery and Medicine).

Primary Examiner—Max Hindenburg
Attorney, Agent, or Firm—Phillips, Moore, Lempio & Finley

[57]    ABSTRACT

An endoscopic laser instrument is adapted to treat selected areas of body tissue, such as the treatment and evaporation of tumors occurring on the inner of a bladder. The instrument comprises an outer tubular sheath having an optical fiber extending therethrough to emit a laser beam onto an adjustable mirror that reflects the laser beam exiting the fiber to selected areas of the bladder without changing the character of divergence of the beam once it has emerged from the fiber. A standard endoscope viewing optic is mounted in the sheath to permit a surgeon to visually inspect the bladder through a wide visual field. A gas, such as carbon dioxide, is continuously circulated through the instrument and into the bladder for inflation and purging purposes.

27 Claims, 6 Drawing Sheets

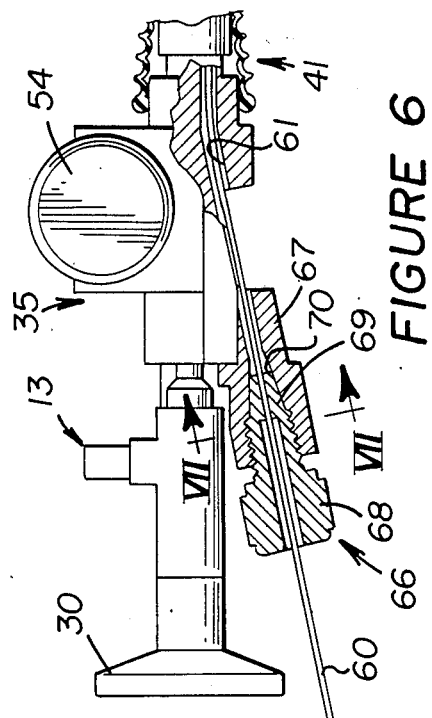
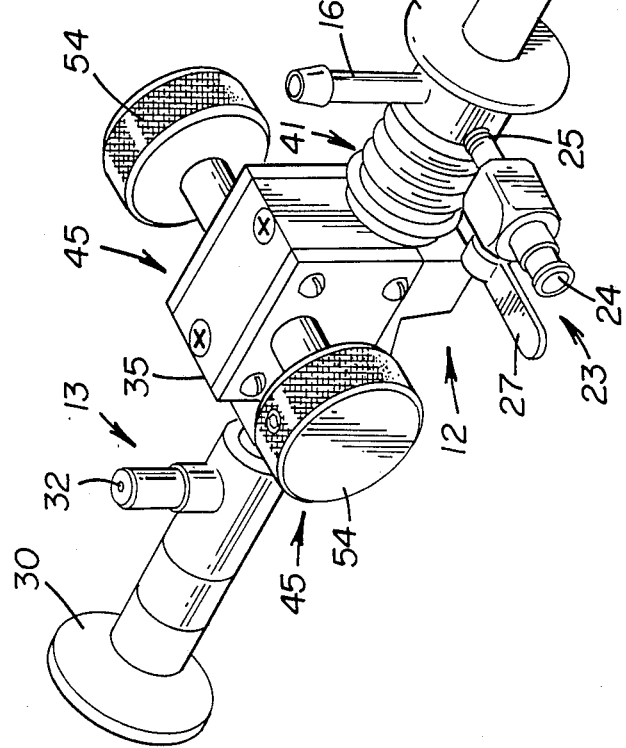
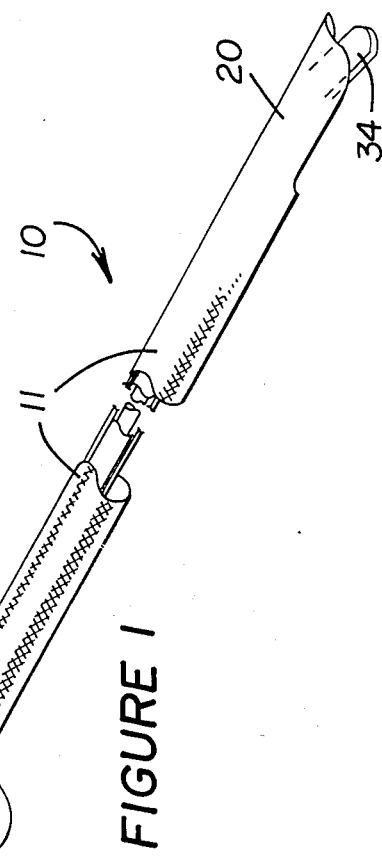
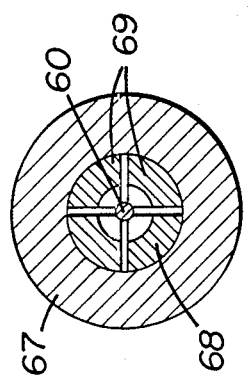
FIGURE 1
FIGURE 6
FIGURE 7

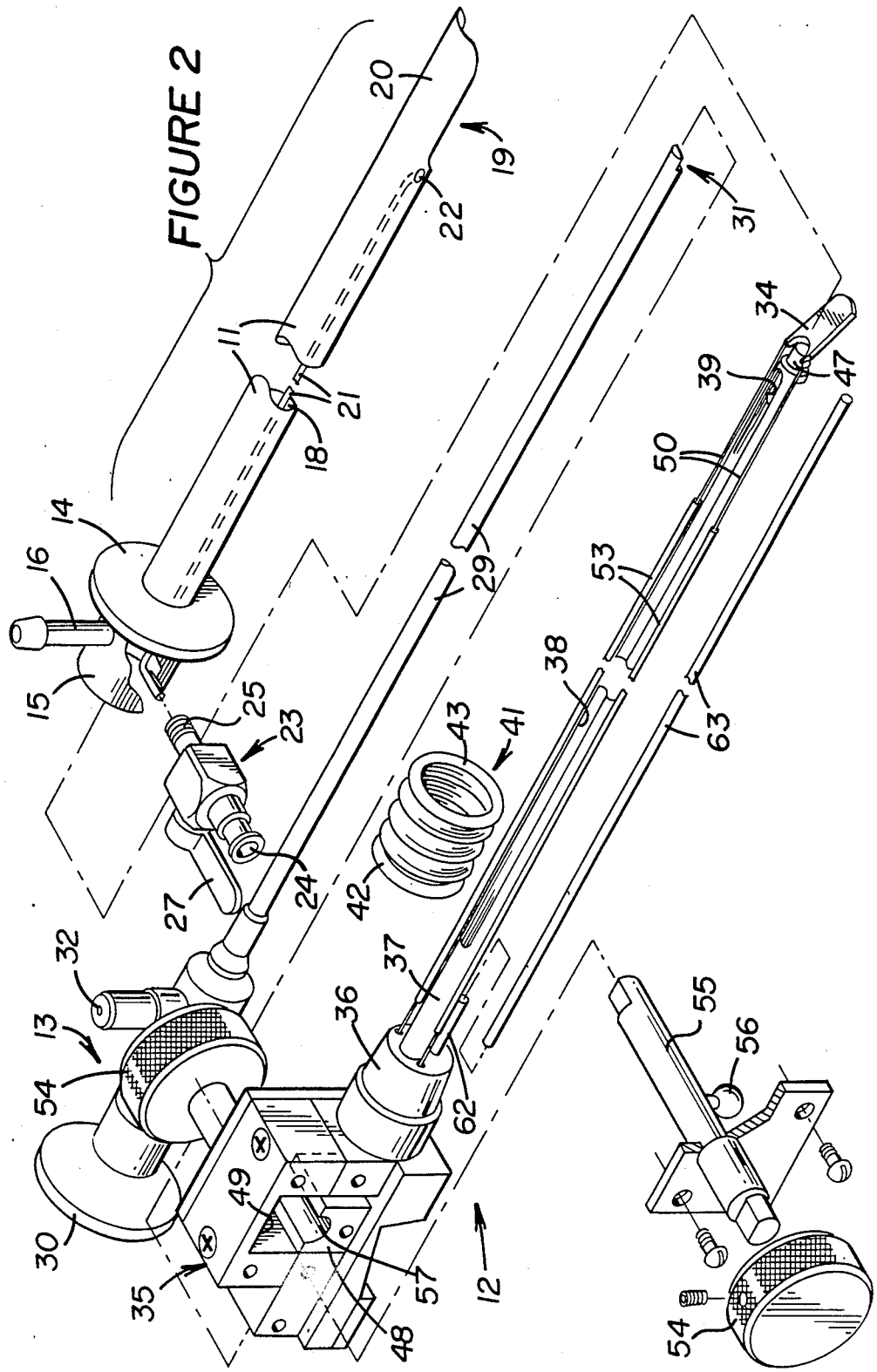

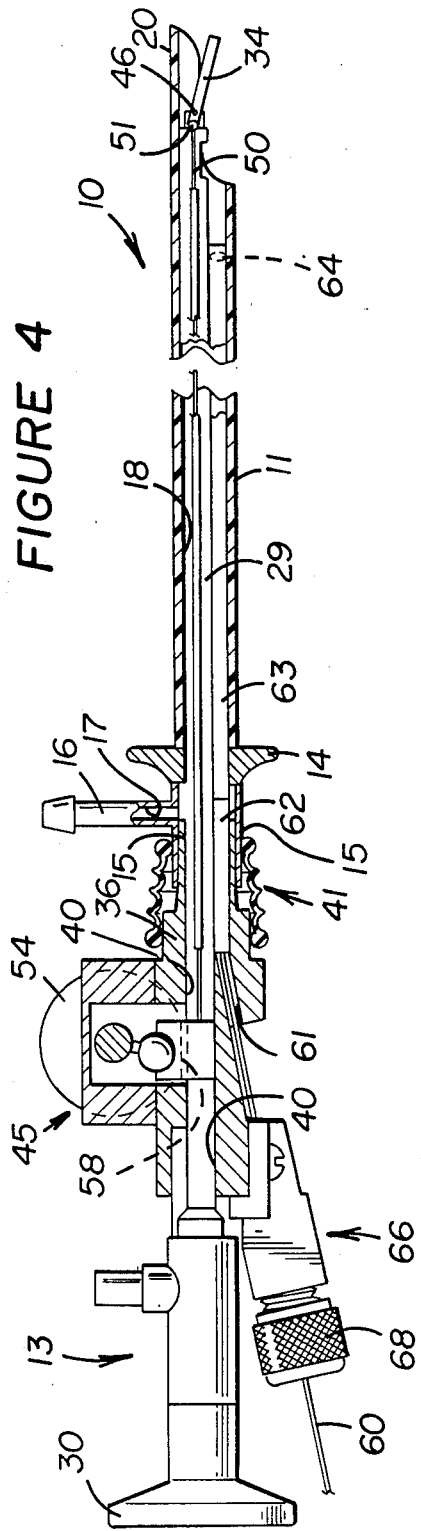
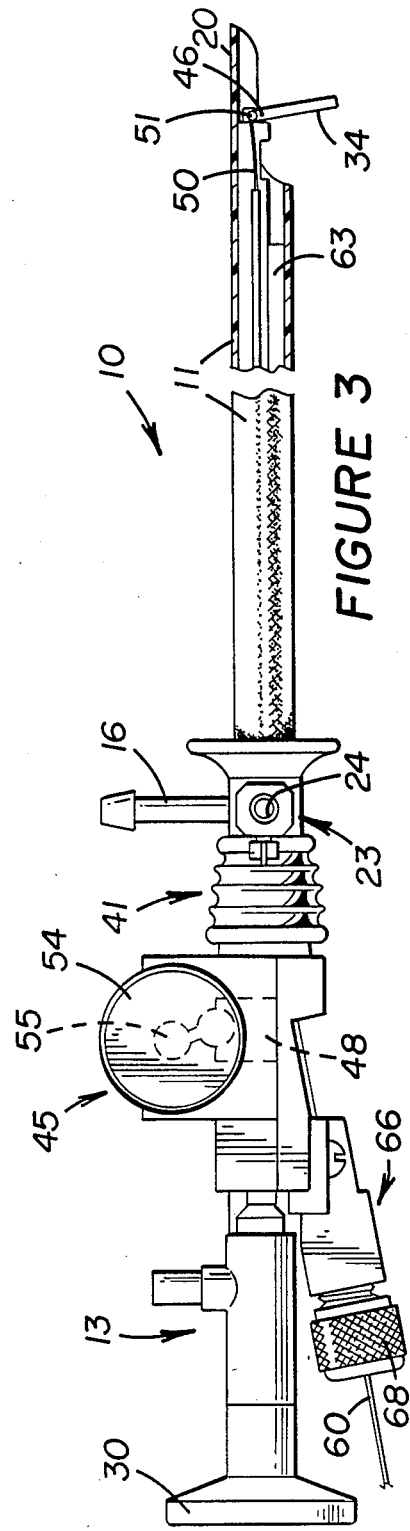

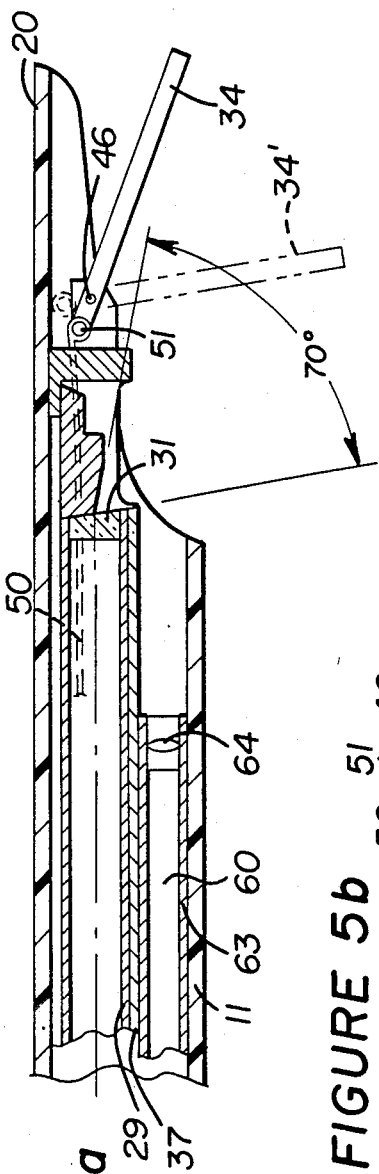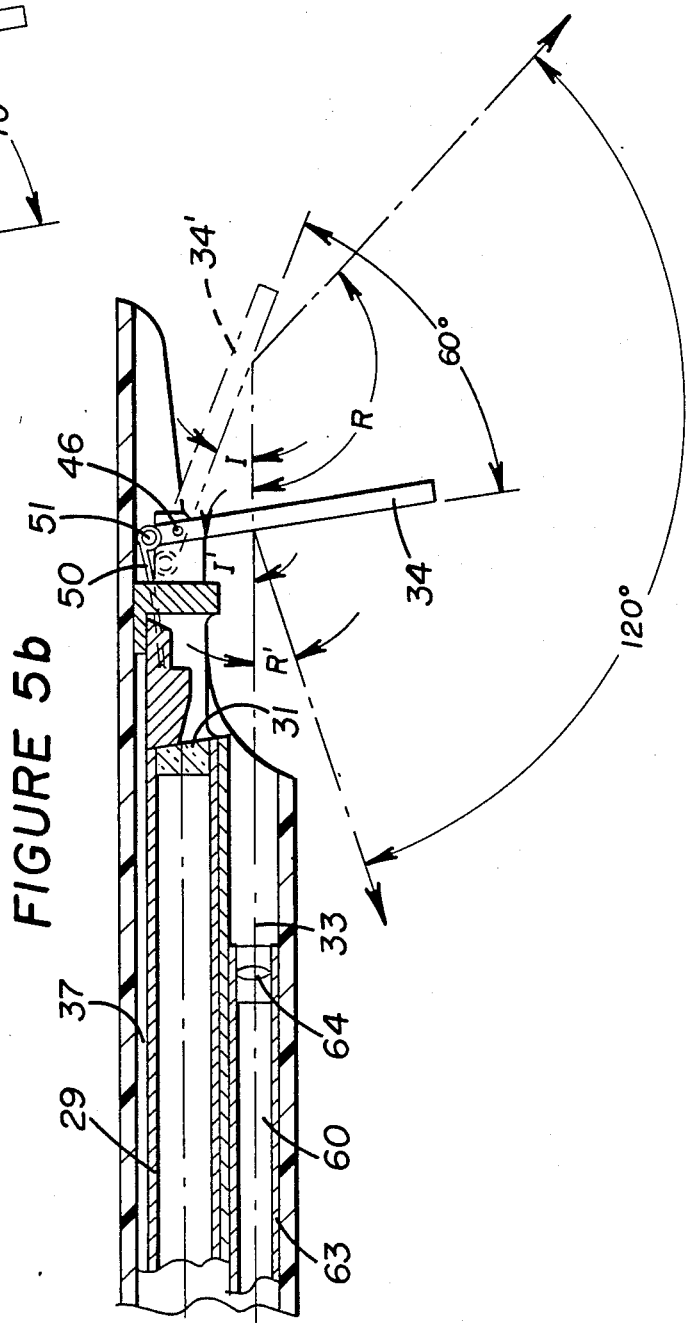

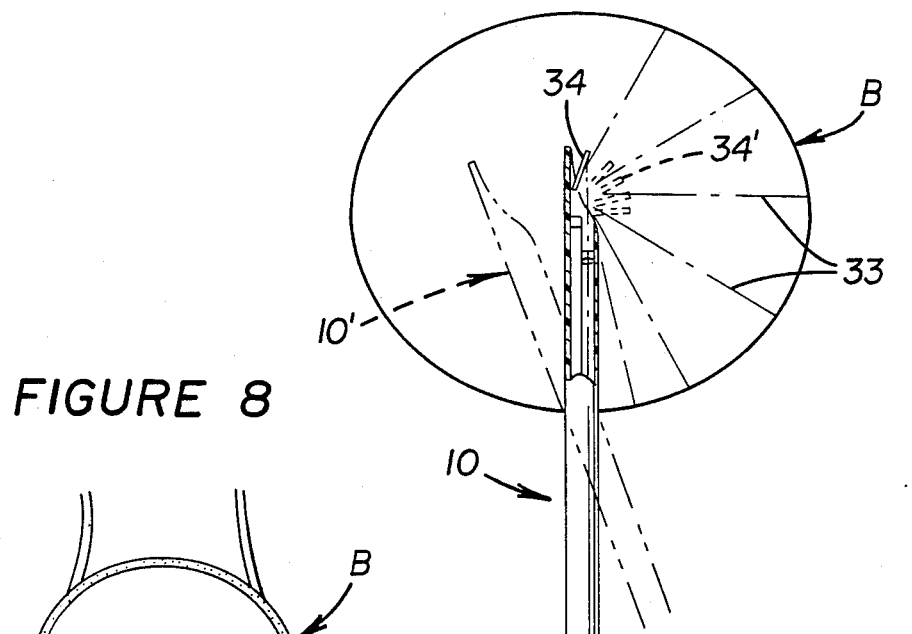
FIGURE 8
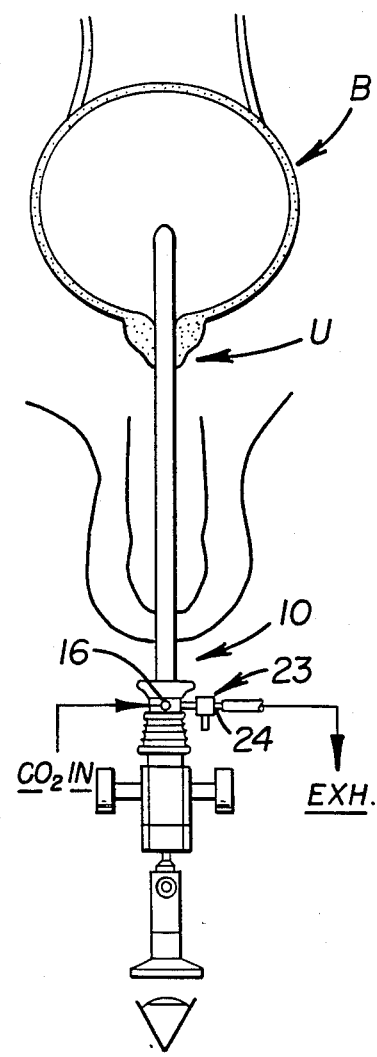
FIGURE 9
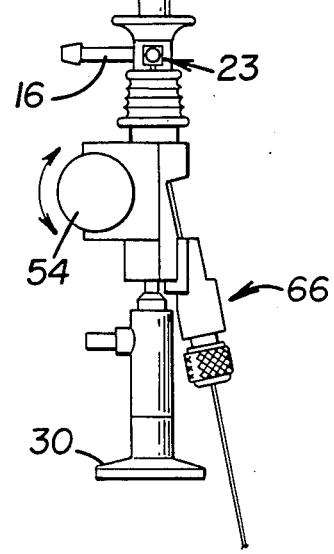

S = Symphysis pubis
P = Prostate

ENDOSCOPIC LASER INSTRUMENT

TECHNICAL FIELD

This invention relates to a laser instrument for endoscopically treating maladies and more particularly to an endoscopic laser instrument adapted to have a laser beam reflected therefrom to treat selected areas of a bladder or the like.

BACKGROUND ART

The use of lasers for endoscopic urologic surgery has been limited primarily to those lasers whose light can be transmitted through glass or quartz optical fibers. Lasers of this type include the synthetic noedymium-doped yttrium aluminum garnet laser crystal (Nd-YAG), argon ion, and argon pumped dye lasers. The pathologic conditions amenable to treatment by these conventional lasers include primary bladder cancer and urethral stricture disease. Obliteration of these lesions is accomplished through thermal coagulation by use of the (Nd-YAG) and argon ion lasers. Argon pumped dye lasers are capable of treating only bladder cancer by destroying cancer cells through cytotoxic photochemical reactions generated in the presence of a photosensitizer, such as hematoporphyrin derivative. The power output of the latter type of laser is insufficient to thermally destroy a lesion under treatment.

To Applicants' knowledge, none of the above types of endoscopic laser instruments and their associated methods of treatment were found to be any more effective than conventional modes of therapy. Currently, transurethral resection with electrocoagulation is the primary treatment for superficial bladder tumors. Approximately sixty percent of the tumors treated by this method alone will re-occur with such reoccurrence being more frequent for those tumors larger than a centimeter in diameter, those that are multifocal or those that have reoccurred previously.

External beam or intravesicle radiation therapy has proven ineffective for the treatment of superficial bladder cancer. Intravesicle chemotherapy, i.e., repeatedly instilling cytotoxic chemotherapeutic agents into a bladder, constitutes a second-line mode of therapy when transurethral resection fails to control recurrences. The latter form of therapy controls recurrences in approximately twenty-five to forty-five percent of the cases, but involves multiple bladder catherizations, extending over a period of up to two years, with weekly catherizations required during the first six weeks of therapy.

In the treatment of superficial urinary bladder cancer, recurrent modes of laser treatment by conventional techniques have proven ineffective for the elimination of recurrence of the disease after treatment as compared with other forms of conventional therapy of the type described above. The (Nd-YAG) laser is suitable for treating selected patients with superficially urinary bladder cancer as outpatients, but may not be cost effective primarily due to the high cost of the laser system required. Argon pumped dye lasers require the presence of a photosensitizer to generate a cytotoxic photochemical reaction in order to destroy cells. A potential advantage of this form of surgery is that the cancer cells or tissue will be destroyed selectively because of the preferential absorption and/or retention of the photosensitizer by the cancer cells or tissue.

To date, it appears that well differentiated superficial cancers, the most common kind, respond poorly to the latter form of therapy. Also, hematoporphyrin derivative, the most widely used photosensitizer, is retained by the skin for approximately two to four weeks to thus require a patient to avoid direct sunlight for at least a four week period of time. Retreatments, if frequent, become vexing to a patient.

The $CO_2$ laser overcomes many of the shortcomings of the other types of above discussed lasers. For example, the $CO_2$ laser is very efficient in terms of power generation, enables laser lesions to heal with a minimal amount of scar formation, does not require a photosensitizer to effect its cytodestructive effects, and is substantially less expensive than the (Nd-YAG) or argon ion laser systems of equivalent power output.

The recently developed irbium doped yttrium aluminum garnet laser (Er-YAG) has some of the advantages of the $CO_2$ laser in that it produces a 2.96 micron wavelength light which is also strongly absorbed by water and thus will probably have the same effect on tissue as the $CO_2$ laser. In addition, the shorter wavelength light can be transmitted through fluoride glass fibers. A disadvantage is limited power generation and the requirement that the laser be pulsed. These latter two disadvantages may be solved with further development.

Various endoscopic instruments have been proposed to take advantage of laser capabilities for the purpose of treating maladies of the type described above. For example, U.S. Pat. No. 4,583,526 discloses an endoscopic instrument that uses a $CO_2$ laser and a bundle of relatively inflexible optic fibers (chalcogenide glass) for performing laser surgery. The instrument is not conducive for optically viewing and surgically treating all portions of the inner wall of a bladder, for example, and will tend to change the character and divergence of the laser beam when the fibers are necessarily bent to the small radii of curvature necessary to effect the surgical procedure.

Similar problems arise in respect to the endoscopic laser instrument disclosed in U.S. Pat. No. 4,313,431 wherein an optical fiber must be bent during use to limit its area of application and adversely change its character and divergence, i.e., change in "spot size" of the laser beam due to bending of the fiber. It should be noted in this respect that the polycrystalline fibers are more prone to deform and/or fracture when they are bent to small radii of curvature, in contrast to more flexible glass fibers used in other types of lasers.

U.S. Pat. No. 4,141,362 discloses an endoscopic laser instrument which attempts to avoid the optical fiber bending problem by positioning a pivotal mirror within the instrument to reflect laser light within the viewing field of the endoscope proper. However, the viewing field as well as the area on which the laser beam can be impinged upon is severely limited. Also, the laser beam apparently passes through an optical window at an oblique angle that changes the beam's character and intensity. In addition, the patent fails to disclose means for insufflating a viscus and evacuating smoke.

DISCLOSURE OF THE INVENTION

This invention provides an improved endoscopic laser instrument for efficiently and effectively treating maladies by tissue evaporation and/or tissue thermal coagulation.

The endoscopic laser instrument of this invention comprises an outer tubular sheath having an endoscope mounted therein for viewing purposes. A laser light transmitting means is also mounted in the sheath that has an end thereof disposed adjacent to an outer end of the sheath for emitting a laser beam from the instrument. Reflecting means, preferably comprising a mirror disposed adjacent to the distal end of the laser transmitting means, receives and reflects the laser beam without changing the character or divergence thereof after it exits the laser transmitting means and impinges upon the area of body tissue to be treated.

Adjustment means are preferably provided for selectively tilting the mirror to widely vary the angle of incidence of the laser beam thereon. Further, gas injection means are provided with the instrument for selectively communicating a pressurized gas, such as carbon dioxide, through the instrument and to a distal end thereof for purposes described hereinafter.

The endoscopic laser instrument is preferably constructed in modular form whereby the sheath can be initially inserted through an urethra to position the distal end thereof within a bladder. A laser assembly, including the laser light transmitting means, reflecting means and adjustment means for selectively tilting a mirror of the reflecting means to reflect the laser beam directly to a tumor or the like, is then telescopically inserted into the sheath. An endoscope assembly is then inserted into and mounted on the laser assembly to provide the surgeon with a viewing field during the laser beam treatment.

BRIEF DESCRIPTION OF THE DRAWINGS

Other objects and advantages of this invention will become apparent from the following description and accompanying drawings:

FIG. 1 is an isometric view illustrating an endoscopic laser instrument embodiment of this invention;

FIG. 2 is an exploded isometric view illustrating component parts of the endoscopic laser instrument;

FIGS. 3 and 4 are partially sectioned side-elevational views of the endoscopic laser instrument showing a laser beam reflecting mirror in two different positions;

FIGS. 5a and 5b are enlarged longitudinal sectional views of an end of the endoscopic laser instrument, showing movement of the mirror between its fully extended (FIG. 5a) and retracted (FIG. 5b) positions;

FIG. 6 is a partially sectioned view of a proximal end of the endoscopic laser instrument, illustrating a clamping device for securing an optical fiber in place thereon;

FIG. 7 is an enlarged sectional view through the clamping device, taken in the direction of arrows V11—V11 in FIG. 6;

FIGS. 8-10 schematically illustrate use of the endoscopic laser instrument for directing a laser beam to various internal areas of a bladder.

BEST MODE OF CARRYING OUT THE INVENTION

Figure 10:
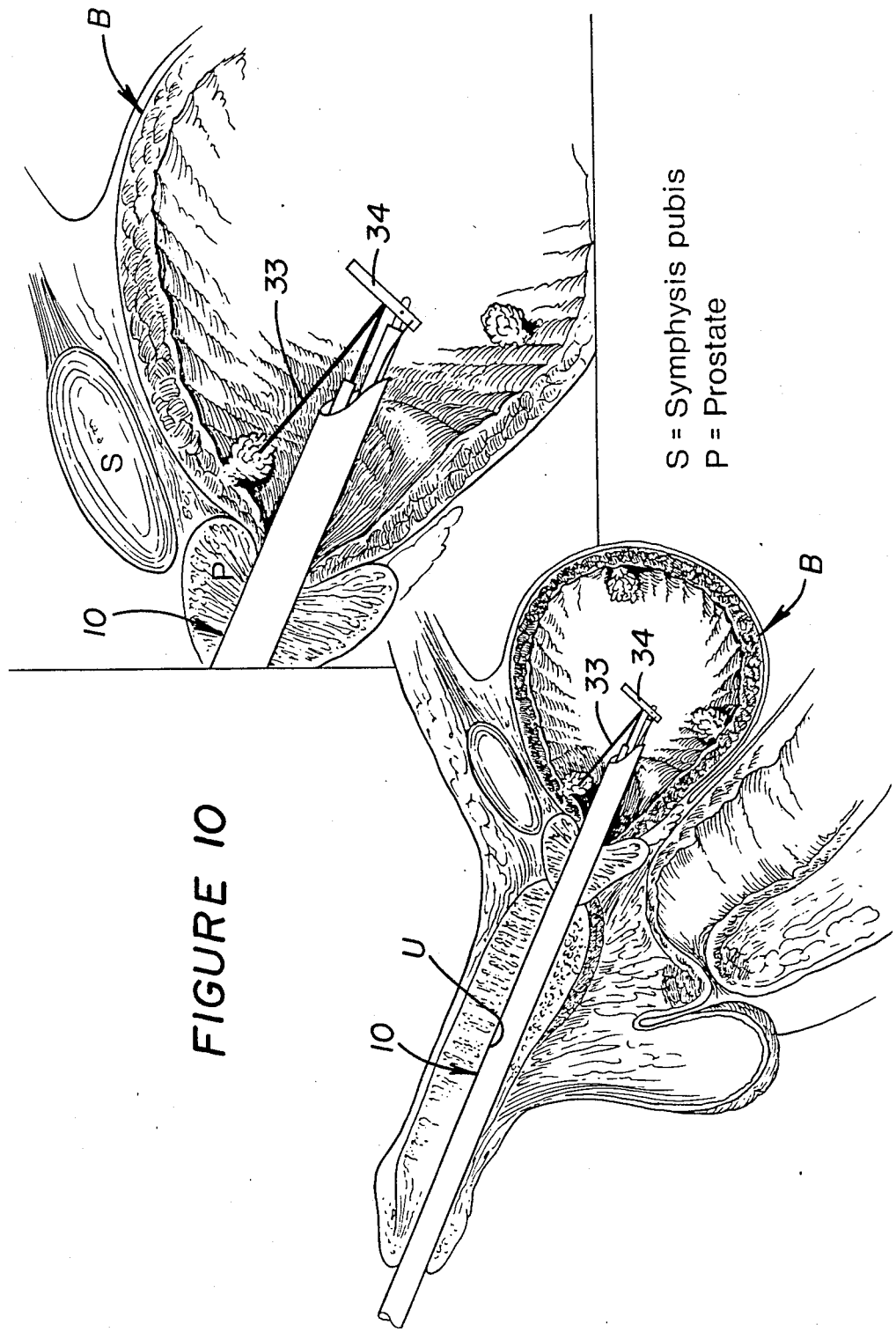

FIGS. 1 and 2 illustrate an endoscopic laser instrument 10 comprising an outer tubular sheath 11 having a laser assembly 12 and an endoscope or viewing assembly 13 telescopically mounted therein. The modular makeup of the instrument facilitates, during a surgical treatment of a bladder, initial insertion of the sheath through the urethra of a patient to position the distal end of the sheath within the patient's bladder. Thereafter, the laser and viewing assemblies are inserted into the sheath for purposes of directing a laser beam to a selected internal area of the bladder (FIGS. 8 and 9) for tissue evaporation and/or tissue thermal coagulation.

As shown in FIGS. 2-4, sheath 11 comprises a tube composed of a reinforced fiberglass, stainless steel or other suitable material having an outer diameter sized for insertion through an urethra. A flange 14 and stainless steel collar 15 are secured on a proximal end of the sheath with the collar having a gas inlet (e.g., $CO_2$) tube 16 secured thereon. As shown in FIG. 4, the inlet tube defines an internal inlet passage 17 that communicates with an internal longitudinal open passage 18 defined throughout the entire length of the sheath.

A distal end 19 of the sheath is cut-away on its bottom side to provide a protective cover 20 for purposes hereinafter explained. A stainless steel exhaust tube 21 (FIG. 2) is fixed within the sheath and terminates at its distal end at an inlet 22, formed through the distal end and sidewall of the sheath. The proximal or outlet end of the tube is connected to a standard two position, one-way valve (stop cock) 23 for selectively exhausting the gas circulated through a bladder from inlet tube 16.

The valve has an outlet 24, a fitting 25 connected to the outlet end of tube 21 and a handle 27 for selectively connecting outlet 24 to exhaust tube 21. Outlet 24 and the upper end of gas inlet tube 16 define standard fittings for connection to standard surgical tubing or the like. The above system thus provides gas circulation means for selectively communicating a gas to a distal end of the instrument and for exhausting the gas and extraneous matters back through the instrument.

Laser assembly 12 includes a number of constructions and arrangements not found on a conventional "bridge" used in association with standard cystoscopes. A conventional cystoscope normally includes a tubular sheath, a telescopic viewing lens (TVL), similar to viewing assembly 13, and a so-called bridge. The bridge defines a lens channel to accommodate the telescopic viewing lens and a second channel that accomodates other instruments, such as catheters or biopsy forceps. Viewing assembly or TVL 13 may be of the standard type manufactured by American Cystoscope Makers, Inc., of New York. The TVL has standard visible light optics which permit visual examination of the inside of a bladder, for example, to thus allow for the direct visual control of all endoscopic manipulations.

The optical system includes a viewing tube 29 having an eyepiece 30 and a viewing lens system 31 (schematically illustrated in FIG. 5 as a single lens) mounted on opposite ends thereof to dispose the lens system adjacent to a distal end of the sheath. The optical or lens system is arranged in a conventional manner to provide the surgeon with a viewing angle approximating 70° (FIG. 5a) and visibility of all internal areas of a bladder when the instrument is manipulated (reciprocated, rotated and/or tilted as shown at position 10' in FIG. 9), as described more fully hereinafter. The standard visible light optics of the TVL includes a fiber optic bundle 32 extending to the distal end of the TVL to conduct ambient light into the bladder or other bodily organ for illumination purposes.

Referring to FIGS. 2-5a and 5b, the laser assembly is adapted to be telescopically mounted in sheath 11 for emitting a laser beam 33 (FIG. 5b) onto a reflecting means, shown in the form of a mirror 34. The mirror is positioned adjacent to distal end 19 of sheath 11 and is protected by cover 20 so that the mirror will not contact bladder tissue when the laser assembly is fully inserted into the sheath. As described more fully hereinafter, the mirror can be titled and adjusted between its solid and phantom line positions 34 and 34', illustrated in FIGS. 5b and 9, to reflect the laser beam to a selected area of body tissue without changing the character or divergence of the laser beam. Simultaneously therewith, the surgeon is enabled to visualize the internal walls of the bladder within a field of vision having a viewing angle approximately 70° (FIG. 5a), for example.

Laser assembly 12 further includes a housing 35 having a generally annular support and guide member 36 extending from a frontal side thereof. A support tube 37 is secured on a frontal side of member 36 to telescopically receive viewing tube 29 of viewing assembly 13 therein. An elongated slot 38 is formed through tube 37 and, along with a smaller slot 39 formed through the support tube at a distal end thereof, functions to aid in the communication of a pressurized gas (e.g., $CO_2$ from inlet tube 16, through the instrument, and into a bladder.

In its assembled condition and as shown in FIGS. 1, 3 and 4, slightly tapered (forwardly) member 36 is slip-fit into sealing engagement within annular collar 15 of sheath 11. As shown in FIG. 4, the distal end of collar 15 is thus positioned to permit free communication between gas inlet passage 17 and passage 18. Viewing tube 29 of viewing assembly 13 is slip-fit through an elongated bore 40 formed through housing 35. An elastomeric bellows 41 has an O-ring seal 42 fixedly mounted on member 36 and a second O-ring seal 43 slip-fit over collar 15. In practice and when laser assembly 12 is inserted into sheath 11, seal 43 can be slipped over collar 15 to provide additional gas and dust sealing desiderata.

FIGS. 1-4 illustrate an adjustment means 45 for selectively adjusting reflecting means or mirror 34, relative to the longitudinal axis of the instrument and laser beam 33 (FIG. 5b), to vary the angle of incidence of the laser beam as it impinges on the mirror. As further shown in FIG. 5b, the adjustment means is enabled to tilt the mirror through an included acute angle approximating 60° between the mirrors retracted solid line position 34 and its extended position 34'. Laser beam 33 will thus impinge on the mirror within a range of incident angles 1 to 1' (FIG. 5b) of approximately 20° to 80°, respectively. The resulting total included reflection angles R and R' (between the lines of incidence and reflection of beam 33) are thus within the approximate range of from 20° to 140°. The illustrated tilting angle of 60° could be, of course, increased up to 90° by obvious modifications to the instrument including a hereinafter described adjustment means 45 for the mirror.

Since the angle of reflection is equal to the angle of incidence, the surgeon is enabled to direct the laser beam to all areas on the internal wall of a bladder, for example. It should be understood that sheath 11 can be reciprocated, rotated for 0° to 360° and/or tipped slightly (e.g., phantom line position 10' of the instrument in FIG. 9) to direct the laser beam to extreme areas directly in front of the instrument and areas adjacent to the instrument whereat it enters the bladder (e.g., see FIG. 10).

One feature of the mirror is its ability to receive and reflect the laser beam without changing the character or divergence thereof. The mirror is may be composed of a substrate material suitably coated to reflect 95-100% of incident laser energy (e.g., a highly polished stainless steel material that is 23 carat gold electroplated) to enable it to reflect a 10.6 micron wavelength light (for a $CO_2$ laser). With the wide degree of laser beam deflection capability, all areas of the inner surface a urinary bladder will be illuminatable, thus allowing treatment of lesions in all of these areas.

The mirror is pivoted by a pin 46 on a distal extension 47 of support tube 37. The ability of the mirror to direct the laser beam in the manner described above distinguishes this instrument from conventional instruments now being used that normally depend on a bending of optical fibers to direct the laser beam. In addition to the inability of the surgeon to bend the fibers more than approximately 22° relative to the normal longitudinal axis of the fibers, due to their brittle nature, bending of the fibers in this manner changes the character and divergence of the beam and the "spot size" as it impinges on a lesion to be treated.

Referring to FIGS. 1-4 and 5b, adjustment means 45 includes a slide block 48 mounted within a cut-out 49 defined in housing 35 for permitting the slide block to be moved back and forth in the direction of the longitudinal axis of the instrument, as shown in FIGS. 3 and 4. A pair of laterally spaced and flexible stainless steel wires 50 have their proximal ends suitably secured to a frontal side of the slide block and their distal ends pivotally connected at pins 51 to an upper end of mirror 34. The wires are guided in their movements by a pair of guide tubes 53, suitably secured on lateral sides of support tube 37.

Wires 50 are selectively reciprocated simultaneously to change the tilting or inclination of mirror 34 by manually turning one of two knobs 54, adapting the instrument for use by either the right or left-hand. The knobs are secured to the opposite ends of a rock shaft 55, rotatably mounted on housing 35. A ball 56, secured under the shaft intermediate its ends, seats within a semi-circular cut-out or socket 57 to thus permit block 48 and wires 50 to be selectively reciprocated under control of knobs 54. As shown in FIG. 4, slide block 48 has a semi-circular cut-out 58 formed on the underside thereof, aligned with bore 40, to accommodate insertion of viewing tube 29 therethrough.

Referring to FIGS. 2-7, laser assembly 12 further includes laser light transmitting means, shown in the form of a standard optical fiber 60. The fiber (the term "optical fiber" is used in the art to define a single fiber or bundle of fibers) extends through a passage 61 formed in housing 35 and further through telescoped tubes 62 and 63 to have its distal end disposed adjacent to and in facing relationship relative to mirror 34.

The fiber may be composed of a standard light conducting material, such as a polycrystalline non-toxic metal halide material, encased in a watertight manner. Optical fiber material of this type is capable of 30-60 percent transmission of the laser light over a one meter length. It is also capable of transmitting sufficient power to obtain output power at the distal end of the fiber in the approximate range of from 10-20 watts. In certain applications and wherein a particular optical fiber exhibits undue divergence, such divergence can be corrected by the use of a removable collimating lens system, schematically shown at 64, secured within the distal end of tube 63, and/or by finely polishing the distal end of the fiber.

A coupler and spacers (not shown) can be utilized to maintain the proper alignment and distance between the distal end or tip of fiber 60 and lens system 64. In one application, the lens material consisted of zinc selenide and antireflective coatings. Other types of lens materials can be used, such as germanium or crystalline sodium chloride mounted in a disposable lens mount.

As shown in FIGS. 4, 6 and 7, the proximal end of optical fiber 60 is releasably secured to housing 35 of laser assembly 12 by a clamping device 66. The clamping device may comprise a bracket 67 secured to housing 35 and a thumb screw 68 threadably mounted on the bracket. As shown in FIGS. 6 and 7, the distal end of thumb screw 68 is tapered and forms four circumferentially spaced split and cantilevered flexible fingers 69 disposed in a tapered socket 70. Thus, when the screw is turned clockwise to thread it into bracket 67, tapered socket 70 will compress fingers 69 radially inwardly towards each other to clamp optical fiber 60 therebetween.

A typical surgical procedure, utilizing endoscopic laser instrument 10, will now be described. For example, the instrument can be used to endoscopically treat various forms of bladder cancer, involving a cancerous tumor on the inner lining of a bladder. Other maladies can obviously be treated with the instrument, such as urethral stricture and congenital ureteropelvic junction obstruction by tissue evaporation and/or tissue thermal coagulation.

Referring to FIGS. 8 and 9, sheath 11 is first inserted through the urethra U of a patient to position the distal end of the sheath within a bladder B. The liquid in the bladder is allowed to drain through the sheath until the bladder is totally evacuated. Laser assembly 12 is then inserted into the sheath and viewing assembly 13 is inserted through housing 35 and into the sheath to a position such that the component parts have almost reached the end of the sheath but have not entered the bladder. The O-ring of bellows 43 is then slipped over collar 15, then $CO_2$ gas is injected into port 16 to partially insufflate the bladder. The laser assembly with the viewing lens in place is then advanced fully into the sheath such that the mirror assembly is fully positioned in the bladder lumen.

The induction of a gaseous atmosphere into the bladder will prevent the laser light from being absorbed, in contrast to a liquid medium which would function to absorb a $CO_2$ laser light. In addition, a continuous flow of the gas into and out of the bladder, via exhaust outlet 24, will evacuate "smoke" occasioned by the burn-off of a tumor or other bodily tissue by the laser light and will maintain the optics (lens system 31 and mirror 35) substantially clean and clear for optical viewing purposes.

The surgeon can then manipulate the instrument (reciprocation, tilting and/or rotation, if necessary) to visually note the location of the tumor via eyepiece 30 and lens system 31. Mirror 34 is then manipulated by knob 54 to direct the laser beam to the tumor to burn and evaporate it. In the case of a $CO_2$ laser, approximately 10 watts of power are required for this purpose. The water composing the tumor (approximately, 90%) will readily absorb the $CO_2$ laser light. In the case of a (ND-YAG) laser, for example, entire slabs of tissue will be heated since the laser light emitted therefrom is essentially absorbed by the proteins which compose approximately 10% of the tissue. It should be understood that laser assembly 12 can be readily adapted to accommodate a $CO_2$, (ND-YAG) or any other required type of laser, even for the purpose of treating the same patient.

As suggested above, the $CO_2$ laser is highly efficient in terms of power generation in that it is capable of converting 10% of power input into usable laser energy as compared to 1% for the (ND-YAG) laser and 0.03% for the argon ion laser. This desirable characteristic of the $CO_2$ laser means that the power source need not be large to generate an output beam of sufficient power to be surgically useful. Also, the beam wavelength (10.6 microns) is strongly absorbed by water which constitutes 90% of a living cell. Thus, when a $CO_2$ laser beam strikes living tissue, most of the energy is attenuated and deposited in the surface layers, causing rapid heating and evaporation of the intracellular water, bursting of the cells, and thus evaporation of the irradiated cell layer.

Deeper layers remain undamaged because the laser energy is dissipated in the form of steam and smoke. The depth of the lesion is thus a function of the power density of the laser beam spot and the time required for irradiation. High power density spots cause rapid evaporation of successive cell layers, forming a crater. Tissues up to 0.5 mm deep to the crater surface will exhibit little, if any, thermal damage. The result is that the $CO_2$ laser lesions heal with minimal scarring.

(Nd-YAG) and argon lasers transilluminate the tissue to a greater degree and deposit their energy to a greater depth in the tissue, leading to thermal coagulation of deeper cell layers without an efficient evaporation of surface layers. Thus, more thermally damaged tissue remains and a greater amount of scarring results during healing of the wound.

Another advantage with the $CO_2$ laser is that a photosensitizer is not required to effect the cytodestructive effects. Thus, all of the common problems associated with the use of photosynthesizers are avoided. Another advantage with the $CO_2$ laser is that its cost is approximately 50% less than the cost of either the YAG or argon ion laser system of equivalent power output.

The $CO_2$ laser is particularly adapted for use with instrument 10, although other types of laser systems can be used therewith. The healing characteristics of $CO_2$ laser wounds offer the hope that different modalities of therapy can be applied to superficial bladder cancer and urethral stricture disease. In the case of superficial urinary bladder cancer, wider areas around the cancer lesion can be treated without the threat of inducing excessive scar formation and thus compromise normal bladder function.

Expansion of the treatment area to include the entire lower hemisphere of the bladder lining, by use of mirror 34, decreases the rate of recurrence by eliminating microscopic areas of tumor formation that otherwise would go untreated by current methods of endoscopic resection or laser coagulation. It has been observed that 80% of superficial bladder cancers occur in the lower bladder hemisphere as a first time occurrence with less than 10% of the lesions occurring in the upper hemisphere. Thus, it is expected that the rate of reoccurrence would be favorably affected if this lower area of the bladder could be treated as a unit in a single operation.

The area involved is too large to be treated in such a manner by current methods. The superficial nature and superior healing characteristics of the $CO_2$ laser induced wounds offers the possibility that this laser system could be used to treat such a large area of a bladder inner lining with minimal compromise in bladder function. In the case of urethral stricture disease, the $CO_2$ laser offers the opportunity to evaporate scar tissue extant in the stricture and that the new wound will heal with less scarring than the original lesion.

Heretofore, the use of the $CO_2$ laser for endoscopic bladder or urethral surgery has been limited by problems unique to the $CO_2$ laser beam. First, the $CO_2$ laser beam is strongly absorbed not only by water, but also by quartz, glass and crystals. Therefore, the laser light cannot be conducted through conventional optical fibers. The recent development of a laser fiber capable of conducting 10.6 micron light has enabled the $CO_2$ laser to be used in instrument 10. The fiber comprises a polycrystalline fiber composed of non-toxic materials exhibiting light transmission in the range of from 50% to 70%. Although the fiber cannot be bent to a radius of curvature of less than 10 centimeters, the fiber is ideally suited for use in the instrument since undue bending of the fiber is not required.

Another previous disadvantage of the $CO_2$ laser is that it could not be used for surgical treatment in the bladder or urethra since liquid contained therein absorbed the energy of the laser beam. As described above, liquid evacuation and the utilization of a steady gas flow (e.g., $CO_2$) through the instrument and into the bladder overcomes the light absorption problem and also provides a medium for the continuous dilution and removal of smoke and steam resulting from tissue evaporation.

We claim:

1. An endoscopic laser instrument, having a longitudinal axis, for treating a selected area of body tissue comprising
   an outer tubular sheath having open proximal and distal ends,
   endoscopic means mounted in said sheath and having an eyepiece and a viewing lens disposed adjacent to the proximal and distal ends of said sheath, respectively, for providing a visual field having a wide viewing angle of at least 30°,
   laser light transmitting means mounted in said sheath and terminating at a distal end thereof disposed adjacent to the distal end of said sheath for emitting a laser beam from said instrument,
   reflecting means, disposed entirely forwardly of and having an area substantially larger than said viewing lens and further disposed adjacent to and in facing relationship relative to the distal end of said laser light transmitting means, for receiving and reflecting said laser beam without changing the character or the divergence thereof after said beam exits said laser light transmitting means and impinges on said selected area of body tissue, said viewing lens disposed longitudinally between the distal end of said laser light transmitting means and said reflecting means to permit said laser beam to intersect said visual field prior to its reflection by said reflecting means, and
   adjustment means for selectively tilting said reflecting means to direct said reflected laser beam within the range of said visual field.

2. The endoscopic laser instrument of claim 1 further comprising gas circulation means for selectively communicating a gas to a distal end of said instrument and for exhausting said gas through said instrument.

3. The endoscopic laser instrument of claim 2 wherein said gas circulation means comprises a tube disposed in said sheath and having inlet and outlet ends, valve means connected to the outlet end of said tube for exhausting a pressurized gas therethrough and an inlet formed through the distal end and a sidewall of said sheath, to dispose said inlet transversely of the longitudinal axis of said instrument, communicating with the inlet end of said tube.

4. The endoscopic laser instrument of claim 3 wherein said sheath defines an open passage longitudinally through said sheath and wherein said gas circulation means further comprises an inlet tube secured on a proximal end of said instrument communicating with said passage.

5. The endoscopic laser instrument of claim 4 wherein said valve means and said outlet tube are mounted on a proximal end of said sheath.

6. The endoscopic laser instrument of claim 1 wherein said laser light transmitting means comprises at least one optical fiber extending from a proximal to a distal end of said instrument and terminating at a distal end thereof aligned with said reflecting means.

7. The endoscopic laser instrument of claim 6 further comprising a housing having the proximal end of said sheath mounted on a frontal side thereof, a protective tube extending from said housing to the distal end of said instrument, and a passage defined in said housing and terminating at a proximal end of said tube, said optical fiber sequentially extending through said passage and said tube.

8. The endoscopic laser instrument of claim 7 further comprising means for releasably clamping said optical fiber to said housing.

9. The endoscopic laser instrument of claim 1 wherein said reflecting means comprises a mirror and wherein said adjustment means is adapted for selectively tilting said mirror, relative to said axis.

10. The endoscopic laser instrument of claim 9 further comprising a housing having the proximal end of said sheath mounted on a frontal side thereof and a support tube slidably mounted in said sheath and having its proximal end secured on the frontal side of said housing, said mirror pivotally mounted on a distal end of said support tube and wherein said adjustment means comprises control means connected to said mirror for selectively tilting said mirror on said support tube at least through an angle approximating 60°.

11. The endoscopic laser instrument of claim 10 wherein said control means comprises a slide block mounted in said housing for reciprocal movement in the direction of said axis, at least one flexible wire interconnected between said slide block and said mirror and means for selectively reciprocating said slide block and wire to tilt said mirror.

12. The endoscopic laser instrument of claim 11 wherein a pair of laterally spaced flexible wires are interconnected between said slide block and said mirror and further comprising a pair of tubes secured on either side of said support tube each having a said flexible wire reciprocally mounted therein.

13. The endoscopic laser instrument of claim 10 further comprising an annular elastomeric seal mounted between the frontal side of said housing and the proximal end of said sheath for forming a gas-tight seal thereat.

14. The endoscopic laser instrument of claim 1 further comprising collimating lens means positioned between the distal end of said laser light transmitting means and said reflecting means for correcting divergence of laser light emitted from said laser light transmitting means.

15. A modular endoscopic laser instrument, having a longitudinal axis, for surgically treating a selected area of body tissue comprising an outer tubular sheath having open proximal and distal ends, a laser assembly mounted on said instrument comprising laser light transmitting means, including at least one optical fiber terminating at a distal end thereof disposed adjacent to the distal end of said sheath, for emitting a laser beam therefrom, reflecting means, including a mirror disposed adjacent to and in facing relationship relative to the distal end of said optical fiber, for receiving and reflecting said laser beam without changing the character or divergence thereof, after said beam exits said optical fiber, and adjustment means for selectively adjusting said mirror, relative to said axis, to vary the angle of incidence of said laser beam on said mirror, and an interchangeable endoscope assembly, slidably mounted in said sheath, comprising an eyepiece and a viewing lens mounted on opposite ends thereof to dispose them adjacent to the proximal and distal ends of said sheath, respectively, for providing a visual field having a wide viewing angle of at least 30°, said mirror disposed entirely forwardly of and having an area substantially larger than said viewing lens and said viewing lens disposed longitudinally between the distal end of said optical fiber and said mirror to permit said laser beam to intersect said visual field prior to its reflection by said mirror.

16. The endoscopic laser instrument of claim 15 further comprising gas circulation means for selectively communicating a gas to a distal end of said instrument and for exhausting said gas, through said instrument.

17. The endoscopic laser instrument of claim 16 wherein said gas circulation means comprises a tube disposed in said sheath and having inlet and outlet ends, valve means connected to the outlet end of said tube for exhausting a gas therethrough and an inlet formed through the distal end and a sidewall of said sheath, to dispose said inlet transversely of the longitudinal axis of said instrument communicating with the inlet end of said tube.

18. The endoscopic laser instrument of claim 17 wherein said sheath defines an open passage longitudinally through said sheath and wherein said gas circulation means further comprises an gas inlet passage defined at a proximal end of said instrument communicating with said passage.

19. The endoscopic laser instrument of claim 15 further comprising a housing having the proximal end of said sheath mounted on a frontal side thereof, a protective tube extending from said housing to the distal end of said instrument, and a passage defined in said housing and terminating at a proximal end of said tube, said optical fiber sequentially extending through said passage and said tube.

20. The endoscopic laser instrument of claim 19 further comprising means for releasably clamping said optical fiber to said housing.

21. The endoscopic laser instrument of claim 15 further comprising adjustment means for selectively tilting said mirror, relative to said axis.

22. The endoscopic laser instrument of claim 21 further comprising a housing having the proximal end of said sheath mounted on a frontal side thereof and a support tube having its proximal end secured on the frontal side of said housing, said mirror pivotally mounted on a distal end of said support tube and wherein said adjustment means comprises control means connected to said mirror for selectively tilting said mirror on said support tube at least approximately through an angle of 60°.

23. The endoscopic laser instrument of claim 22 wherein said control means comprises a slide block mounted in said housing for reciprocal movement in the direction of said axis, at least one flexible wire interconnected between said slide block and said mirror and means for selectively reciprocating said slide block and wire to tilt said mirror.

24. The endoscopic laser instrument of claim 23 wherein a pair of laterally spaced flexible wires are interconnected between said slide block and said mirror and further comprising a pair of tubes secured on either side of said support tube each having one of said flexible wires reciprocally mounted therein.

25. The endoscopic laser instrument of claim 22 further comprising an annular elastomeric seal mounted between the frontal side of said housing and the proximal end of said sheath for forming a gas-tight seal thereat.

26. The endoscopic laser instrument of claim 15 further comprising collimating lens means positioned between the distal end of said fiber and said mirror for correcting divergence of laser light emitted from said laser light transmitting means.

27. An endoscopic laser instrument, having a longitudinal axis, for treating a selected area of body tissue comprising.

an outer tubular sheath having open proximal and distal ends, and an endoscope assembly slidably mounted in said sheath and comprising a tubular member having an eyepiece and a viewing lens mounted on opposite ends thereof to dispose them adjacent to the proximal and distal ends of said sheath, respectively, for providing a visual field having a wide viewing angle of at least 30°, laser light transmitting means mounted in said sheath and terminating at a distal end thereof disposed adjacent to the distal end of said sheath for emitting a laser beam from said instrument, reflecting means, including a mirror disposed entirely forwardly of and having an area substantially larger than said viewing lens and further disposed externally of said sheath adjacent to and in facing relationship relative to the distal end of said laser transmitting means, for receiving and reflecting said laser beam without changing the character or divergence thereof after said laser beam exits said laser light transmitting means, said viewing lens disposed longitudinally between the distal end of said laser light transmitting means and said mirror to permit said laser beam to intersect said visual field prior to its reflection by said mirror, and adjustment means for selectively tilting said mirror through an angle of at least approximately 60° to direct said reflected laser beam within the range of said visual field, said reflecting means and said adjustment means forming a separate assembly slidably mounted in said sheath.

* * * * *